United States Patent [19]
Goudie et al.

[11] Patent Number: 5,095,127
[45] Date of Patent: Mar. 10, 1992

[54] PROCESS FOR PRODUCING POLYCYCLIC ETHER ANTIBIOTICS

[75] Inventors: Alexander C. Goudie, Ramsgate; Nigel D. A. Walshe, Deal, both of United Kingdom

[73] Assignee: Pfizer Inc., New York, N.Y.

[21] Appl. No.: 628,802

[22] Filed: Dec. 17, 1990

Related U.S. Application Data

[62] Division of Ser. No. 482,367, Feb. 20, 1990, Pat. No. 4,992,466, which is a division of Ser. No. 280,771, Dec. 6, 1988, Pat. No. 4,912,130, which is a division of Ser. No. 76,427, Jul. 21, 1987, Pat. No. 4,804,680.

[30] Foreign Application Priority Data

Aug. 1, 1986 [GB] United Kingdom ............ 8618844

[51] Int. Cl.⁵ .................................. C07D 309/10
[52] U.S. Cl. ................................... 549/343
[58] Field of Search ........................ 549/343

[56] References Cited

U.S. PATENT DOCUMENTS 4,293,650 10/1981 Florent et al. ............ 549/343
4,359,583 11/1982 Mitzutani et al. .......... 549/343
4,565,862 1/1986 Foley et al. ............. 536/16.8

FOREIGN PATENT DOCUMENTS 0169011 1/1986 European Pat. Off. .
53-21170 2/1978 Japan .

Primary Examiner—Nicky Chan
Attorney, Agent, or Firm—Peter C. Richardson; J. Trevor Lumb; Mervin E. Brokke

[57] ABSTRACT

A new acidic polycyclic antibiotic UK-61,689 has the formula:

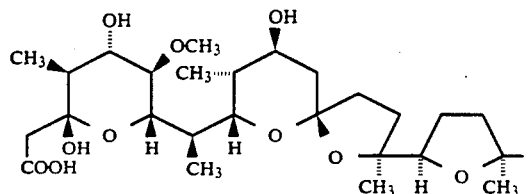

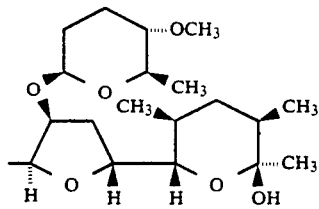

or a pharmaceutically acceptable cationic salt thereof. The antibiotic and its cationic salts are active against a variety of microorganisms and are effective in controlling coccidiosis, enteritis and swine dysentery as well as being effective in promotion of growth and/or improving efficiency of feed utilization in swine and ruminants.

2 Claims, No Drawings

PROCESS FOR PRODUCING POLYCYCLIC ETHER ANTIBIOTICS

CROSS-REFERENCE TO RELATED APPLICATIONS

This application is a division of application Ser. No. 07/482,367, filed Feb. 20, 1990, now U.S. Pat. No. 4,992,466 which is a division of application Ser. No. 07/280,771, filed Dec. 6, 1988, now U.S. Pat. No. 4,912,130, which is a division of application Ser. No. 07/076,427, filed July 21, 1987, now U.S. Pat. No. 4,804,680.

BACKGROUND OF THE INVENTION

The present invention relates to a new member of the acidic polycyclic ether group of antibiotics, a class of compounds characterized biologically by their effect on cation transport across cell membranes. This family of antibiotics includes such well known agents as monensin, nigericin, grisorixin, dianemycin, meduramycin, narasin, salinomycin, lasalocid, mutalomycin, ionomycin and leuseramycin. The subject has been reviewed by Westley, "Polyether Antibiotics", *Adv. Appl. Microbiol.*, 22, 177, 1977.

The polycyclic ether antibiotics listed above are active against Gram-positive bacteria, fungi and protozoa. In particular these antibiotics exhibit potent anti-coccidial activity. They have therefore been employed with varying degrees of success in the treatment of a variety of animal infections.

The well-known protozoan disease, coccidiosis, continues to be a serious problem and its control is of economic importance to veterinary science, especially to the poultry industry. Coccidiosis results from infection by one or more species of Eimeria or Isospora (for a summary, see Lund and Farr in "Diseases of Poultry," 5th ed., Biester and Schwarte, Eds., Iowa State University Press, Ames, Ia., 1965, pp. 1056–1096). There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. There other species of protozoa belonging to the same genus are considered to be relatively innocuous; however, *E. mitis, E. hagani* and *E. praecox* are capable of reducing weight gain, lowering feed efficiency and adversely affecting egg production.

In view of the great economic losses due to coccidiosis, the search for new anticoccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "overeating disease" in sheep, is a condition caused by *C. perfringens* infection.

Swine dysentery is one of the most common swine diseases diagnosed in the United States. Additionally, the disease is prevalent in many other countries and annually causes considerable losses in stock to swine growers around the world. It has recently been discovered that a large spirochete is the causative organism of the disease. This organism, *Treponema hyodysenteriae*, has now been isolated and shown to be capable of producing the disease [Harris, D. L. et al. "Swine Dysentery-1, Inoculation of Pigs with *Treponema hyodysenteriae* (New Species) and Reproduction of the Disease," *Vet. Med/SAC*, 67, 61–64, 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Micro-organisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. For a more detailed discussion, see Leng in "Physiology of Digestion and Metabolism in the Ruminant," Phillipson et al., Eds., Oriel Press, Newcastle-upon-Tyne, England, 1970, pp. 408–410.

The relative efficiency of volatile fatty acid utilization is discussed by McCullough in "Feedstuffs", June 19, 1971, page 19; Eskeland et al. in *J. An. Sci.*, 33, 282, 1971; and Church et al. in "Digestive Physiology and Nutrition of Ruminants", Vol. 2, 1971, pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

The present invention is concerned with a new acidic polycyclic ether antibiotic. EPA-0169011 discloses an acidic polycyclic ether antibiotic designated as UK-58,852 having the formula:

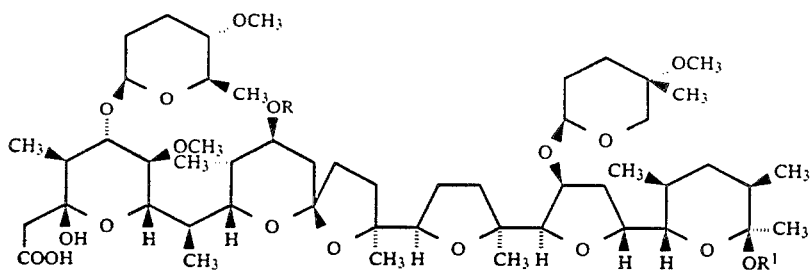

wherein R and R¹ are both H, which is produced by the submerged aerobic propagation in aqueous nutrient media of the microorganism *Actinomadura roseorufa* Huang sp. nov., ATCC 39697 isolated from a soil sample from Japan. It has now been found that hydrolysis of UK-58,852 under carefully controlled conditions leads to the cleavage of one of the attached glycone rings to produce a new compound which is fully effective as a broad spectrum anti-coccidial and which has advantages over UK-58,852 compound because of its improved toxicity profile.

SUMMARY OF THE INVENTION

Thus according to the present invention there is provided a compound designated Antibiotic UK-61,689 of the formula:

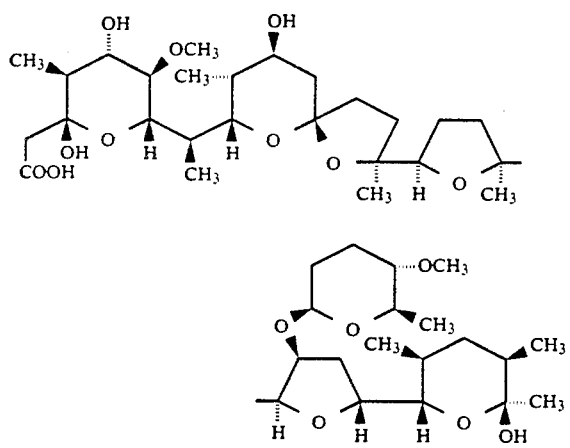

and its pharmaceutically acceptable cationic salts. Examples of such salts are the sodium and potassium salts.

Also according to the present invention there are provided processes for preparing Antibiotic UK-61,689 or a cationic salt thereof which comprise controlled hydrolysis of the compound UK-58,852 or a cationic salt thereof.

DETAILED DESCRIPTION OF THE INVENTION

The hydrolysis of UK-58,852 is preferably carried out using para-toluene sulphonic acid in an acetonitrile/water solvent. The preferred acetonitrile/water composition contains 5 and 0.5% water. Preferably a ratio of 1.1 molar equivalents of para-toluenesulphonic acid to one equivalent of the sodium salt of UK-58,852 is used.

Other solvent systems which may be used include neat acetonitrile or t-butanol/water or acetone/water. Alternative acids include mineral acids such as hydrochloric acid, acetic acid or a strong acid resin. Generally the reaction is carried out at room temperature and is monitored by thin layer chromatography until the yield of the desired product appears to be optimal. The reaction time is generally about one to three hours for the para-toluene sulphonic acid in acetonitrile/water hydrolysis system but will vary depending on the acid and solvent system used. After the reaction has gone substantially to completion, the reaction mixture is neutralized with excess sodium bicarbonate, concentrated and extracted with diethyl ether or dichloromethane and then purified using standard silica gel chromatography techniques. The final product may then be recrystallised as the free acid or appropriate cationic salt.

Alternatively, Antibiotic UK-61,689 may be generated from crude fermentation extracts containing UK-58,852. Thus a methyl isobutylketone (MIBK) fermentation extract is concentrated and preferably dissolved in acetonitrile/water and treated with para-toluenesulfonic acid. The preferred acetonitrile water composition contains 5% water, and the ratio of crude fermentation oil to para-toluenesulfonic acid is about 9:1; these ratios are approximate and may vary according to the composition of the fermentation extract. Other solvent systems which may be used include methanol/water, but the hydrolysis may also be carried out by treating the crude MIBK extract with para-toluenesulfonic acid in the absence of added solvent. Alternative acids include mineral acids such as hydrochloric acid.

Antibiotic UK-61,689 exhibits inhibitory action against the growth of a number of Gram-positive microorganisms. In Table I, below, the results of in vitro tests are summarized. For this test each organism is inoculated in a series of test tubes containing nutrient medium and varying concentrations of Antibiotic UK-61,689 to determine the minimal concentration of the compound in $\mu g./ml.$ which inhibits the growth of the organism over a period of 24 hours (MIC).

TABLE I

| ANTIBACTERIAL ACTIVITY | | |
|---|---|---|
| Organism | Strain No. | MIC $\mu g/ml$ |
| *Clostridium perfringens* | 10A006 | 25 |
|  | 10A009 | 3.12 |
| *Actinomyces pyogenes* | 14D002 | 0.39 |
|  | 14D008 | 0.39 |
|  | 14D011 | 0.39 |
| *Treponema hyodysenteriae* | 94A001 | 6.25 |
|  | 94A002 | 6.25 |
|  | 94A007 | 3.12 |
|  | 94A008 | 3.12 |

Efficacy data for Antibiotic UK-61,689 and its salts against coccidial infections in chickens were obtained in the following fashion. Groups of 3-5 ten-day old pathogen free white leghorn cockerel chicks were fed a mash diet containing Antibiotic UK-61,689 or its sodium and- /or potassium salt uniformly dispersed therein. After being on this ration for 24 hours each chick was inoculated per os with oocysts of the particular species of Eimeria being tested. Other groups of 3-5 ten-day old chicks were fed a similar mash diet without Antibiotic UK-61,689 or its salts. They were also infected after 24 hours and served as infected controls. Yet another group of 3-5 ten-day old chicks were fed the same mash diet without Antibiotic UK-61,689 and were not infected with coccidia. These served as normal controls. The results of treatment were evaluated after five days in the case of E. acervulina, and six days for all other challenges.

The criteria used to measure anticoccidial activity consisted of lesion scores of 0 to 4 for E. tenella after J. E. Lynch, "A New Method for the Primary Evaluation of Anticoccidial Activity", *Am. J. Vet. Res.*, 22, 324-326, 1961; and 0 to 3 for the other species based on modification of the scoring system devised by J. Johnson and W. H. Reid, "Inticoccidial Drugs. Lesion Scoring Techniques in Battery and Floor Pen Experiments in Chicks", *Exp. Parasit.*, 28, 30-36, 1970. A constant ratio was established by dividing the lesion score of each treated group by the lesion score of the infected control.

It was found that Antibiotic UK-61,689 and its cationic salts exhibit excellent activity against coccidial infections in poultry. When incorporated into the diet of chickens at levels of 15 to 120 ppm, these compounds are effective in controlling infections due to *Eimeria tenella, E. acervulina, E. maxima, E. brunetti* and *E. necatrix.*

The value of animal feeds has generally been determined directly by feeding the animal. British Patent Specification No. 1,197,826 details an in vitro rumen technique whereby the changes occurring in feed brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch + 17% cellulose + 15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml. of the sample is mixed with 1 ml. of 25% metaphosphoric acid. After 10 minutes 0.25 ml. of formic acid is added and the mixture centrifuged at 1500 rpm for 10 minutes. Samples are then analyzed by gas-liquid chromatography by the method of D. W. Kellog, *J. Dairy Science*, 52, 1690, 1969. Peak heights for acetic, propionic and butyric acids are determined for samples from untreated and treated incubation flasks.

When tested by this in vitro procedure, Antibiotic UK-61,689 at the level of 20 micrograms per milliliter gave rise to an increase of about 80% in the production of propionic acid over that produced in the control solution without added Antibiotic UK-61,689. Compounds which stimulate the production of RPA (Rumen propionic acid) are known to improve feed utilization by ruminants such as cattle and sheep, and can also have a similar effect on monogastric animals such as pigs. Antibiotic UK-61,689 can be administered to the animal by incorporation into feed compositions, either as the free acid or as a salt e.g. the sodium or potassium salt, or a mixture thereof. Alternatively, a crude form or dried fermentation broth containing antibiotic UK-61,689 can be incorporated in feed composition at the desired potency concentrations. Antibiotic UK-61,689 can also be administered at the desired dosage using an appropriate sustained release device designed to meter out constant levels of drug.

For use in the treatment of coccidiosis in poultry the compound of this invention is administered orally in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed iteslf; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements may be added directly to the poultry feed to produce a nutritionally balanced, finished feed containing a therapeutically effective level of the compound of this invention. The mixtures are thoroughly blended by standard procedures, such as in a twin shell blender, to ensure homogeneity.

It will, of course, be obvious to those skilled in the art that the use levels of the compound described herein will vary under different circumstances. Continous low-level medication, during the growing period; that is, during the first 6 to 12 weeks for chickens, is an effective prophylactic measure. In the treatment of established infections, higher levels may be necessary to overcome the infection. The use level in feed will generally be in the range of 15 to 120 ppm. When administered in drinking water, the level will be that which will provide the same daily dose of medication, i.e. 15 to 120 ppm, factored by the weight ratio of the average daily consumption of feed to the average daily consumption of water.

The present invention is illustrated by the following examples. However, it should be understood that the invention is not limited to the specific details of these examples.

EXAMPLE 1

To a solution of 15.0 g (0.0147 moles) of pure antibiotic UK-58,852 (prepared as described in EPA 0169011) in acetonitrile/water (95:5) (400 ml) was added 3.07 g (0.0161 moles) of p-toluenesulfonic acid. The reaction was monitored by thin layer chromatography until the yield of the desired product appeared to be optimal (about 3 hours). The reaction mixture was treated with excess solid or aqueous sodium bicarbonate, and concentrated to dryness under vacuum. The resulting solid was dissolved in diethyl ether and washed with a saturated aqueous solution of sodium bicarbonate, the bicarbonate washings were extracted with diethyl ether and all the ether layers were combined and washed successively with water and saturated sodium chloride. The ether solution was dried over anhydrous sodium sulphate and evaporated to dryness under vacuum. The resulting crude reaction product contained UK-61,689 as the predominent product, but was contaminated with varying amounts of starting UK-58,852, and other by-products. The crude product was purified by silica gel chromatography, followed by recrystallization from isopropyl ether to give 4.2 g (32%) of UK-61,689 as the sodium salt, m.p., 175°-176° C.; $[\alpha]_D^{25} = +19.3°$ (c=0.5, MeOH); C-13 NMR (CDCl$_3$): 179.15 ppm, 107.45, 103.18, 97.74, 96.96, 86.92, 84.60, 84.20, 82.27, 82.01, 80.88, 80.20, 79.86, 74.80, 74.55, 73.07, 70.06, 67.71, 66.89, 59.11, 56.81, 45.40, 39.82, 38.93, 36.46, 33.81, 33.71, 33.54, 33.42, 33.13, 32.44, 32.26, 30.56, 27.58, 26.90, 26.84, 26.11, 23.23, 18.40, 17.53, 16.9 9, 12.13, 11.04, 10.42.

EXAMPLE 2

A crude fermentation extract (MIBK) (1 1.) containing the antibiotic UK-58,852 (estimated 25 g) was concentrated under vacuum to 680 g. The thick dark oil was added to acetonitrile/water (95:5) (5.6 1.), and the resulting milky emulsion was treated with p-toluenesulfonic acid (78.2 g) in one portion. As the reaction proceeded, the emulsion gradually separated into two distinct layers which were stirred vigorously for a total of 1.25 hours. The reaction mixture was poured into a separatory funnel, and the oily bottom layer was removed and slurried with additional acetonitrile/water (95:5). The acetonitrile/water layers were combined and treated with saturated aqueous sodium bicarbonate (400 ml). The mixture was then concentrated to a thick syrup under vacuum, dissolved in diethyl ether/ethyl acetate (3:1) (2 1.) and washed with saturated aqueous sodium bicarbonate. The organic layer was dried over sodium sulfate and concentrated to a thick brown oil (432 g). Purification was most conveniently accomplished using counter-current extraction techniques. The extraction employed hexane:ethyl acetate (1:1) as the non-polar phase and methanol:water (3:2) as the polar aqueous phase. Evaporation of the organic extracts gave a semi-solid which was triturated with isopropyl ether to give UK-61,689 as the sodium salt, 10 g, m.p. 169°-170° C. This material was identical to the compound UK-61,689 produced by the method in Example 1, by TLC and NMR comparisons.

We claim:

1. A process for producing an antibiotic of the formula

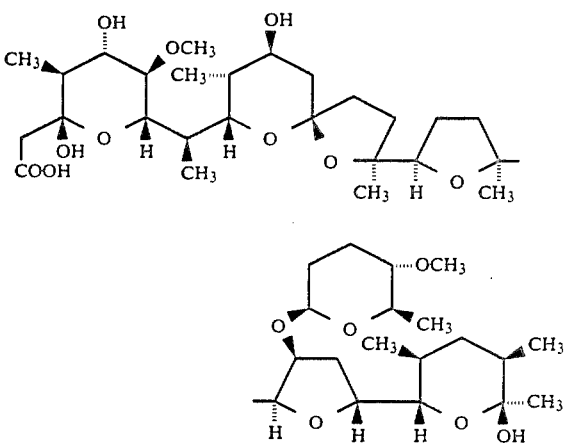

or a pharmaceutically acceptable cationic salt thereof, characterized by the controlled hydrolysis of a compound of the formula

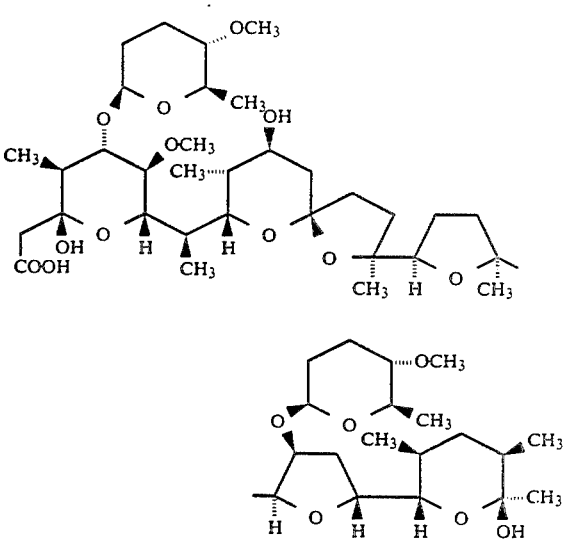

or a cationic salt thereof.

2. A process for producing an antibiotic of the formula

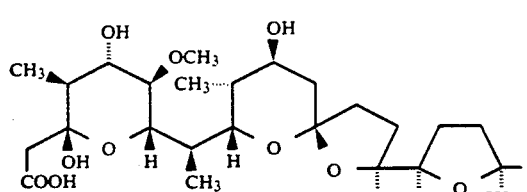
or a pharmaceutically acceptable cationic salt thereof, characterized by the controlled hydrolysis of a compound of the formula
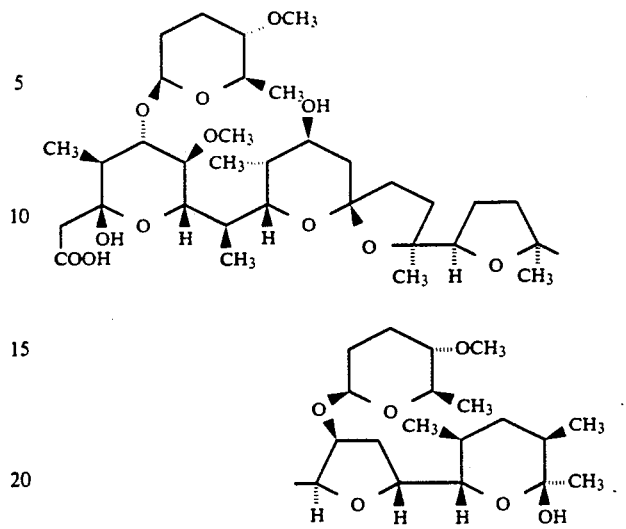
or a cationic salt thereof wherein the hydrolysis is carried out using para-toluene sulphonic acid in an acetonitrile/water solvent.
* * * * *